United States Patent
Dhainaut et al.

(10) Patent No.: US 6,790,967 B2
(45) Date of Patent: Sep. 14, 2004

(54) PROCESS FOR THE PREPARATION OF VITAMIN E

(75) Inventors: Jildaz Dhainaut, Lyons (FR); Thierry Durand, Ecully (FR)

(73) Assignee: Adisseo France S.A.S., Antony (FR)

( * ) Notice: Subject to any disclaimer, the term of this patent is extended or adjusted under 35 U.S.C. 154(b) by 0 days.

(21) Appl. No.: 10/323,273

(22) Filed: Dec. 19, 2002

(65) Prior Publication Data

US 2003/0153772 A1 Aug. 14, 2003

Related U.S. Application Data

(62) Division of application No. 09/787,264, filed as application No. PCT/FR99/02196 on Sep. 15, 1999, now Pat. No. 6,518,439.

(30) Foreign Application Priority Data

Sep. 18, 1998 (FR) .............................................. 98 11679

(51) Int. Cl.$^7$ ............................................. C07D 311/04
(52) U.S. Cl. ....................... 549/400; 549/410; 549/411; 549/412
(58) Field of Search ................. 549/400, 410, 549/411, 412

(56) References Cited

U.S. PATENT DOCUMENTS

| | | | |
|---|---|---|---|
| 3,708,505 A | 1/1973 | Greenbaum et al. | 260/345.5 |
| 5,663,376 A | 9/1997 | Hirose et al. | 549/411 |
| 5,886,197 A | 3/1999 | Hirose et al. | 549/411 |
| 5,900,494 A | 5/1999 | Bonrath | 549/411 |
| 5,908,939 A | 6/1999 | Baak et al. | 549/407 |
| 6,005,122 A | 12/1999 | Baldenius et al. | 549/410 |
| 6,020,505 A | 2/2000 | Hirose et al. | 549/411 |

FOREIGN PATENT DOCUMENTS

| | | |
|---|---|---|
| CZ | 205951 | 5/1981 |
| EP | 0087576 | 9/1983 |
| EP | 0694541 A | 1/1996 |
| EP | 0782993 | 7/1997 |
| EP | 0850937 | 7/1998 |
| EP | 0924208 | 6/1999 |
| FR | 2126214 | 10/1972 |
| JP | 51080859 | 7/1976 |
| JP | 59190987 | 10/1984 |
| JP | 60054380 | 3/1985 |
| JP | 58171248 | 4/1985 |
| JP | 62226976 | 10/1987 |
| WO | 9821197 | 5/1998 |

OTHER PUBLICATIONS

U.S. patent application No. 09/787,264, filed May 14, 2001, Dhainaut, et al., "Method for Preparing Vitamin E," Examiner Andrea Small, Art Unit 1626.
English language abstract for JP 59190987 (Oct. 1984).
English language abstract for JP 60054380 (Mar. 1985).
English language abstract for EP 0850937 (Jul. 1998).
English language abstract for JP 62226976 (Oct. 1987).
English language abstract for EP 0924208 (Jun. 1999).
English language abstract for JP 58171248 (Apr. 1985).

*Primary Examiner*—Deborah C. Lambkin
*Assistant Examiner*—Andrea D. Small
(74) *Attorney, Agent, or Firm*—Connolly Bove Lodge & Hutz LLP

(57) ABSTRACT

The invention concerns a novel method for preparing vitamin E. More particularly, it concerns a novel method for the condensation of trimethylhydroquinone and isophytol.

15 Claims, No Drawings

PROCESS FOR THE PREPARATION OF VITAMIN E

CROSS-REFERENCE TO RELATED APPLICATION

The present application is a divisional of, and claims the benefit of, U.S. patent application Ser. No. 09/787,264, which was filed on May 14, 2001, now U.S. Pat. No. 6,518,939 in the name of Jildaz Dhainaut, et al., and was entitled Method for Preparing Vitamin E which is the National Stage of PCT/FR99/02196, filed Sep. 15, 1999

The present invention relates to a novel process for the preparation of vitamin E. It relates more particularly to a novel process for the condensation of trimethylhydroquinone and isophytol.

It is known, for example according to Japanese Patents No. 60064977, No. 53144574 and No. 53015381, to condense isophytol with trimethylhydroquinone in the presence of a Lewis acid, restricted to zinc chloride, in the presence of an inorganic acid chosen from halogenated acids and polyphosphoric acid in a solvent composed of methylene chloride and acetic acid.

It is also known, from Japanese Patents No. 59190987 and No. 48072168, to condense trimethylhydroquinone with isophytol in the presence of a catalyst based on zinc chloride and of an acid chosen from hydrochloric acid or trichloroacetic acid; the reaction being carried out in a solvent composed of an acetyl ester and in particular of isopropyl acetate.

Finally, it is known, from Japanese patent No. 48072167, to condense isophytol with trimethylhydroquinone under the same conditions as above but removing the water of the reaction as it is formed during the condensation. Japanese Patent No. 6226976, which carries out the reduction of trimethylhydroquinone and the condensation with isophytol in the same solvent as above, that is to say isopropyl acetate, eliminates the presence of water between the two stages so as to avoid the presence of water during the final condensation of trimethylhydroquinone with isophytol.

The present reaction can be represented schematically in the following way:

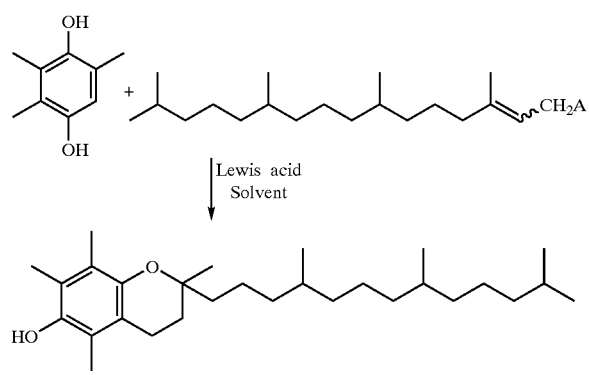

in which scheme A represents a halogen atom, a hydroxyl group or an acetoxy group.

It has transpired, entirely surprisingly, that, if it is desired to restrict the consumption of TMHQ to 1 molar eq. with respect to isophytol, the presence of water in the condensation stage has a favourable effect on the reaction, contrary to that suggested by all of this prior art. The water prevents side reactions of TMHQ at the beginning of the running in of isophytol.

Furthermore, it is known, according to Patent EP 0 850 937, that it is possible to condense TMHQ with isophytol in the presence of water provided that a nonpolar solvent, such as an alkane, is used. The maximum amount of water which can be used without harming the reaction yield and without distilling off the water formed during the reaction is limited to 1.5 mol of water per mole of isophytol. Under these conditions, the influence of the amount of zinc chloride used was not studied.

It has transpired that, when the process described previously is carried out, that is to say when the catalysis with zinc chloride was carried out in the absence of water and in a polar solvent, such as esters, there was a significant loss of TMHQ by transesterification with the solvent. The present invention has made it possible to overcome this problem and has made it possible to carry out the condensation of TMHQ with isophytol in a polar solvent of the ester type and in the presence of water.

The present invention thus consists in carrying out the condensation of a phytol with trimethylhydroquinone in a polar solvent of the ester type and in the presence of a Bronsted acid and of a zinc halide, characterized in that the reaction is carried out in the presence of an amount of water of between 0.7 molar eq. and 2 molar eq. with respect to the number of moles of zinc halide and in the presence of an amount of zinc halide of greater than 0.3 molar equivalent with respect to the phytol.

The presence of this amount of water has numerous advantages;
  it makes it possible to increase the reaction yield by approximately 4%,
  it makes it possible to recycle the zinc halide,
  at equivalent stoichiometry for TMHQ and phytol, the presence of water increases the yield,
  it prevents the esterification of TMHQ by the solvent.

Furthermore, in the case of solvents from the family of the esters, in contrast with the case of the hydrocarbons disclosed in Patent EP 0 850 937, the presence of water requires the use of amounts of zinc halides of greater than 0.3 molar equivalent with respect to phytol, so as:
  to retain a yield>92%
  to accelerate the kinetics of the reaction.

The phytol is chosen from isophytol or a phytyl halide, such as phytyl bromide, phytyl chloride or phytyl acetate.

The reaction is carried out in particular in the presence of a Bronsted acid chosen from hydrochloric acid or sulphuric acid. It is preferable to use hydrochloric acid.

The reaction is carried out in the presence of a polar solvent which makes it possible to dissolve trimethylhydroquinone and the phytol used. Mention may be made, among polar solvents which may be used, of esters and among these of ethyl, propyl, isopropyl, butyl or isobutyl acetate; acetates having a longer chain are not preferred although they can be used; the viscosity of the solvent simply increases with the length of the chain, which is not very favourable to the reaction. Esters of longer organic acids than the acetates can also be used, in particular esters of propionic, butyric or isobutyric, valeric or isovaleric acid, but, as in the case of the acetates, the increase in the length of the chain increases the viscosity of the medium, which is not always favourable to the reaction. It is preferable, among all these esters, to use isopropyl acetate.

The presence of water in the reaction medium, which improves the condensation yield, leads in some cases to the presence of a two-phase system. In this case, it is advantageous to add an organic acid chosen from acetic acid, propionic acid or butyric acid in order to prevent the phases from separating. It is preferable to use the acid corresponding to the ester used as solvent. Thus, when an acetate is used, it is preferable to add acetic acid.

The amount of organic acid added corresponds to approximately 3 to 20 times the amount by weight of water present in the medium.

The catalyst used to promote the condensation is chosen from zinc halides. It is preferable to use zinc chloride. It is advantageous also to use a Bronsted acid chosen from hydrochloric acid or sulphuric acid.

According to a better way of implementing the invention, the catalyst is used according to a ratio of approximately 0.7 to 1.2 equivalents per mole of phytol.

The advantage of using this amount of Lewis acid with respect to the prior art, which uses less thereof, is:

to increase the reaction rate, to improve the selectivity of the condensation.

The molar ratio of the hydroquinone to the phytol is preferably between 1 and 1.5 and it is highly preferably between 1 and 1.2. The Bronsted acid is preferably used according to a molar amount of between 4% and 16% with respect to the number of moles of phytol.

For a better implementation of the invention, it is preferable to operate at a temperature of between 55° C. and 75° C.

The α-tocopherol obtained is separated from the reaction medium by liquid/liquid extraction.

The following stage of the process for the preparation of vitamin E, when it is provided in the acetate form, consists in carrying out the acetylation of the α-tocopherol.

This stage is carried out according to a novel method which consists in acetylating the α-tocopherol with acetic anhydride in the absence of any solvent, that is to say neat.

The acetylation is carried out in the presence of a catalyst composed of an inorganic acid chosen from sulphuric acid or phosphoric acid or of an alkaline acetate.

It has been discovered that it is preferable to employ phosphoric acid or sodium acetate as it is possible, with these catalysts, to completely avoid colouring the reaction medium during the acetylation. The tocopheryl acetate obtained is even lighter than the starting tocopherol. It is preferable to use a molar ratio of the acetic anhydride to the tocopherol of between 1 and 1.8. Use if preferably made of 0.7 to 2 molar % of acid as acetylation catalyst when the latter is sulphuric acid, 1 to 2 molar % when the acetylation catalyst is phosphoric acid and 5 to 10 molars when the acetylation catalyst is sodium acetate.

The present invention also relates to a complete process for the preparation of vitamin E from trimethylbenzoquinone, the entire process being carried out in the same solvent, which is a good solvent for trimethylbenzoquinone, for trimethylhydroquinone and for the phytol. This solvent is in particular a polar solvent, preferably an ester and highly preferably isopropyl acetate.

It consists, in a first stage, in carrying out a hydrogenation of trimethylbenzoquinone with a hydrogenation catalyst, preferably a supported catalyst, chosen from palladium and platinum. It is preferable to use palladium supported on charcoal.

The second stage consists, after filtration so as to remove the catalyst, in carrying out the condensation of the trimethylhydroquinone obtained in the first stage with the phytol under the conditions described above and in particular in the presence of a zinc halide, of a Bronsted acid and of water and very particularly in the presence of zinc chloride, of hydrochloric acid and of water. At the end of the reaction, the catalyst is extracted with water and this aqueous phase is concentrated, in particular from 80 wt % to 91 wt % of $ZnCl_2$, so as to leave at most, including the water from the Bronsted acid, only two moles of water per mole of zinc halide recycled to the second stage of the process.

The organic phase is then preferably concentrated to dryness, so as to remove the reaction solvent and its possible by-products, and then acetylated neat as described above.

The process for the extraction of vitamin E acetate is subsequently carried out conventionally and in a way known to a person skilled in the art. The medium is extracted with a solvent which is immiscible or virtually immiscible with water, then washed with an acid solution, so as to hydrolyze the remaining acetic anhydride, and then washed in alkaline medium, to deacetylate the TMHQ acetates. The aqueous phase comprising the alkaline salt of TMHQ is isolated by a two-phase separation, this phase is acidified and the TMHQ is extracted with the reaction solvent, that is to say the ester, which allows it to be recycled to the condensation stage.

The invention will be more fully described with the help of the following examples, which should not be regarded as limiting the invention.

EXAMPLES

Preparation of TMHQ in Solution by Hydrogenation

Example 1

3.1 g of Pd/c (3%, 52% $H_2O$) and 3 550 g of IPAC are charged to an 8 1 hydrogenation reactor rendered inert beforehand with nitrogen. The reactor is placed under 0.5 bar of hydrogen with stirring. The medium is heated to 80° C. and is maintained at this temperature for 10 minutes.

The reactor is subsequently pressurized to 2 bar of hydrogen. Hydrogenation is carried out semi-continuously by simultaneous addition of 96.5% w/w TMBQ (total charge= 700.3 g) and of hydrogen, so as to remain at 80° C. and under 2 bar of hydrogen. The end of the reaction is detected by the fall in the hydrogen flow rate.

The reaction medium is degassed and then purged with nitrogen. The reaction medium is filtered while hot under nitrogen pressure. The solution of 708.2 g of TMHQ in IPAC is obtained which is ready for use in the condensation reaction. The hydrogenation yield is 99.8%.

TMHQ/Isophytol Condensation Reactions in the Absence of Water

Example 2

A hot solution of 76 g of TMHQ in IPAC comprising 16% w/w of IPAC is charged with stirring to a 1 l reactor. This solution is concentrated with stirring to 38% w/w by distillation of IPAC at 45° C. under vacuum. 50.1 g of 98% w/w $ZnCl_2$, dissolved in 72 g of acetic acid under warm conditions, are added to the suspension obtained, followed by 4 g of 92% w/w of sulphuric acid. The reaction medium is heated to 75° C. 162 g of 91.5% w/w isophytol are then run in over 43 min. After the isophytol has finished being run in, the reaction is maintained at 75° C. for 60 min. 100 g of water are charged with stirring and the mixture is subsequently separated by settling. The volatile products are removed from the organic phase by distillation at 75° C. under vacuum. 1 g of 92% w/w sulphuric acid is charged at 75° C. and then 88.5 g of 98% w/w acetic anhydride are run in at this temperature over 10 min. The reaction medium is heated to 105° C. over 20 min and then rapidly cooled to 35°

C. 1 200 g of hexane are charged with stirring, followed by 71 g of water. The two phases are separated by settling. The organic phase is again washed with 71 g of water. The organic phase is evaporated on a rotary evaporator at 60° C. under vacuum for 2 h.

254.8 g of crude 84.2% w/w tocopheryl acetate (Toco) are obtained (yield=90.9%).

The procedure of Example 3 is identical to that of Example 2. Only the running-in time changes (84 min). The parameters are shown in Table 1.

the reaction is maintained at 75° C. for 60 min. 100 g of water are charged with stirring and the mixture is subsequently separated by settling. The volatile products are removed from the organic phase by distillation at 75° C. under vacuum. 1.1 g of 92% w/w sulphuric acid are charged at 75° C. and then 88.6 g of 98% w/w acetic anhydride are run in at this temperature over 10 min. The reaction mixture is heated to 105° C. over 30 min and then rapidly cooled to 35° C. 120 g of hexane are charged with stirring, followed by 70 g of water. The two phases are separated by settling.

TABLE 1

Influence of the absence of water.

| Example | Maintenance time (min) | AcOH (g) | $ZnCl_2$ (eq)* | Acid (eq) | T (° C.) | $H_2O$ (g) | Total $H_2O$** (mol/mol $ZnCl_2$) | Toco assay (%) | Toco Yd (% pure/pure) |
|---|---|---|---|---|---|---|---|---|---|
| 2 | 60 | 72 | 0.72 | $H_2SO_4$ (0.08) | 75 | 0 | 0.05 | 84.2 | 90.9 |
| 3 | 60 | 72 | 0.72 | $H_2SO_4$ (0.08) | 75 | 0 | 0.05 | 81.9 | 87.2 |

TMHQ/Isophytol = 1 molar eq.
*the equivalents are in moles with respect to the number of moles of isophytol
**total $H_2O$ = $H_2O$ + $H_2O$ present in 92% $H_2SO_4$.

TMHQ/Isophytol Condensation Reactions in the Presence of Water

Reactions with Acid=36% HCl Without Addition of Additional Water

Example 4

A hot solution of 76 g of TMHQ in IPAC comprising 16% w/w of IPAC is charged with stirring to a 1 l reactor. This solution is concentrated with stirring to 38% w/w by distillation of IPAC at 45° C. under vacuum. 50.1 g of 98% w/w $ZnCl_2$, dissolved in 72 g of acetic acid under hot conditions, are added to the suspension obtained, followed by 8.1 g of 36% w/w hydrochloric acid. The reaction medium is heated to 75° C. 161.6 g of 91.6% w/w isophytol are then run in over 47 min. After the isophytol has finished being run in, The organic phase is again washed with 70 g of water. The organic phase is evaporated on a rotor evaporator at 60° C. under vacuum for 2 h.

258 g of crude 86.4% w/w tocopheryl acetate (Toco) are obtained (yield=94.3%).

The procedures of Examples 5 and 6 are identical to that of Example 4. The parameters modified in the examples are specified in Table 2.

TABLE 2

Influence of the presence of water.

| Example | Maintenance time (min) | AcOH (g) | $ZnCl_2$ (eq)* | Acid (eq) | T (° C.) | $H_2O$ added (g) | Total $H_2O$** (mol/mol $ZnCl_2$) | Toco assay (%) | Toco Yd (% pure/pure) |
|---|---|---|---|---|---|---|---|---|---|
| 4 | 60 | 72 | 0.72 | 36% HCl (0.16) | 75 | 0 | 0.75 | 86.4 | 94.3 |
| 5 | 60 | 72 | 0.72 | 36% HCl (0.16) | 75 | 0 | 0.75 | 87.8 | 93.4 |
| 6 | 90 | 47 | 0.45 | 36% HCl (0.09) | 62 | 0 | 0.75 | 89.5 | 97 |

TMHQ/Isophytol = 1 molar eq.
*the equivalents are in moles with respect to the number of moles of isophytol
**total $H_2O$ = $H_2O$ + $H_2O$ present in 36% HCl.

TMHQ/Isophytol Condensation Reactions in the Presence of Water

Reactions with Acid=36% HCl or 92% $H_2SO_4$ with Addition of Water

Influence of the Water Content and of the $ZnCl_2$ Stoichiometry

Example 7

A hot solution of 76 g of TMHQ in IPAC comprising 16% w/w of IPAC is charged with stirring to a 1 l reactor. This solution is concentrated with stirring to 38% w/w by distillation of IPAC at 45° C. under vacuum. 50.1 g of 98% w/w $ZnCl_2$, dissolved in 72 g of acetic acid under warm conditions, 4.28 g of 92% w/w sulphuric acid and 5 g of water are added to the suspension obtained. The reaction mixture is heated to 75° C. 162 g of 91.5% w/w isophytol are then run in over 40 min. After the isophytol has finished being run in, the reaction is maintained at 75° C. for 60 min. 200 g of water are charged with stirring and the mixture is subsequently separated by settling. The volatile products are removed from the organic phase by distillation at 75° C. under vacuum. 1.1 g of 92% w/w sulphuric acid are charged at 75° C. and then 88.5 g of 98% w/w acetic anhydride are run in at this temperature over 10 min. The reaction medium is heated to 105° C. over 30 min and is then rapidly cooled to 35° C. 200 g of hexane are charged with stirring, followed by 50 g of water. The two phases are separated by settling. The organic phase is again washed with 30 g of water. The organic phase is evaporated on a rotary evaporator at 60° C. under vacuum for 2 h.

253.2 g of crude 88.2% w/w tocopheryl acetate (Toco) are obtained (yield=94.6%).

The procedures of Examples 8 to 15 are identical to that of example 7. The sulphuric acid is sometimes replaced by hydrochloric acid. The parameters modified in the examples are specified in Table 3.

TABLE 3

Influence of the water content and of the $ZnCl_2$ stoichiometry.

| Example | Maintenance time (min) | AcOH (g) | $ZnCl_2$ (eq)* | Acid (eq) | T (° C.) | $H_2O$ (g) | Total $H_2O$** (mol/mol $ZnCl_2$) | Toco assay (%) | Toco Yd (% pure/pure) |
|---|---|---|---|---|---|---|---|---|---|
| 7 | 60 | 72 | 0.72 | $H_2SO_4$ (0.08) | 75 | 5 | 0.75 | 88.2 | 94.6 |
| 8 | 60 | 0 | 0.72 | $H_2SO_4$ (0.04) | 75 | 11 | 1.65 | 86.6 | 93.8 |
| 9 | 120 | 18 | 0.18 | 36% HCl (0.08) | 75 | 0 | 1.5 | 83.2 | 90.1 |
| 10 | 40 | 36 | 0.36 | $H_2SO_4$ (0.04) | 75 | 2.5 | 0.75 | 93.4*** | 95.5 |
| 11 | 60 | 66 | 0.63 | $H_2SO_4$ (0.063) | 62 | 4.3 | 0.75 | 89.6 | 98.4 |
| 12 | 60 | 47 | 0.45 | $H_2SO_4$ (0.045) | 62 | 3.07 | 0.75 | 89.4 | 98.3 |
| 13 | 80 | 40 | 0.72 | 36% HCl (0.15) | 62 | 2.8 | 1.12 | 90.6 | 97.5 |
| 14 | 80 | 0 | 0.45 | 36% HCl (0.09) | 62 | 3.07 | 1.5 | 88.3 | 95.4 |
| 15 | 90 | 45 | 0.72 | 36% HCl (0.09) | 62 | 9.6 | 1.88 | 87.8 | 95.8 |

TMHQ/Isophytol = 1 molar eq.
*the equivalents are in moles with respect to the number of moles of isophytol
**total $H_2O$ = $H_2O$ + $H_2O$ present in the acid
***After partial purification TMHQ/Isophytol Condensation Reactions in the Presence of Water Influence of the TMHQ and $ZnCl_2$ Stoichiometry Example 16

A hot solution of 76 g of TMHQ in IPAC comprising 16% w/w of IPAC is charged with stirring to a 1 l reactor. This solution is concentrated with stirring to 38% w/w by distillation of the IPAC at 45° C. under vacuum. 49.8 9 of 98% w/w $ZnCl_2$, dissolved in 45 g of acetic acid under warm conditions, 4.7 g of 36% w/w hydrochloric acid and then 4.8 g of water are added to the suspension obtained. The reaction mixture is heated to 72° C. 160.5 g of 92.2% w/w isophytol are then run in over 20 min. After the isophytol has finished being run in, the reaction is maintained at 72° C. for 40 min. 100 g of water are charged with stirring and the mixture is subsequently separated by settling. A second washing is carried out with 60 g of water. The volatile products are removed from the organic phase by distillation at 75° C. under vacuum. 0.6 g of 92% w/w sulphuric acid are charged at 85° C. and then 68 g of 92% w/w acetic anhydride are run in at this temperature over 6 min. The reaction medium is maintained at this temperature for 60 min and then rapidly cooled to 35° C. 240 g of hexane are charged with stirring, followed by 220 g of water and by 9 g of 92% w/w $H_2SO_4$. The two phases are separated by settling. The organic phase is then washed with a mixture of 100 g of water and 12 g of 50% NaOH. The organic phase is evaporated on a rotor evaporator at 60° C. under vacuum for 2 h.

After evaporation of partial purification, 232.7 g of 94.8% w/w tocopheryl acetate (Toco) are obtained (yield=93.3%).

The residual TMHQ is recovered by acidification of the alkaline aqueous phase with 92% w/w $H_2SO_4$ and then extraction with IPAC. The solution of recovered TMHQ in IPAC can be recycled in the TMHQ/Isophytol condensation.

The procedures of Examples 17 to 19 are identical to that of Example 16. The parameters modified in the examples are specified in Table 4.

TABLE 4

Influence of the water content and of the $ZnCl_2$ stoichiometry.

| Example | Maintenance time (min) | AcOH (g) | TMHQ (eq) | $ZnCl_2$ (eq)* | Acid (eq) | T (° C.) | $H_2O$ (g) | Total $H_2O$** (mol/mol $ZnCl_2$) | Toco assay (%) | Toco Yd (% pure/pure) |
|---|---|---|---|---|---|---|---|---|---|---|
| 16 | 40 | 45 | 1.01 | 0.72 | 36% HCl (0.09) | 72 | 4.8 | 1.12 | 94.7*** | 93.3 |
| 17 | 40 | 45 | 1.05 | 0.72 | 36% HCl (0.09) | 75 | 4.8 | 1.12 | 95*** | 95.7 |
| 18 | 20 | 45 | 1.15 | 0.72 | 36% HCl (0.09) | 75 | 4.8 | 1.12 | 93.2*** | 96.2 |
| 19 | 40 | 62 | 1.15 | 1 | 36% HCl (0.09) | 75 | 7.6 | 1.12 | 96.4*** | 98 |

*the equivalents are in moles with respect to the number of moles of isophytol
**total $H_2O$ = $H_2O$ + $H_2O$ present in the acid
***After partial purification TMHQ/Isophytol Condensation Reactions in the Presence of Water Recycling of $ZnCl_2$ Example 20

A hot solution of 76 g of TMHQ in IPAC comprising 16% w/w of IPAC is charged with stirring to a 1 l reactor. This solution is concentrated with stirring to 38% w/w by distillation of the IPAC at 45° C. under vacuum. 49.8 g of 98% w/w $ZnCl_2$, 45 g of acetic acid, 4.6 g of 36% w/w hydrochloric acid and then 4.8 g of water are added to the suspension obtained. The reaction medium is heated to 62° C. 161.6 g of 91.6% w/w isophytol are then run in over 60 min. After the isophytol has finishing being run in, the reaction is maintained at 62° C. for 50 min. 100 g of water are charged with stirring and the mixture is subsequently separated by settling. A second washing is carried out with 60 g of water. In all, 269.7 g of aqueous phase comprising more than 99.5% of the $ZnCl_2$ charged are recovered. The volatile products are removed from the organic phase by distillation at 75° C. under vacuum. 0.7 g of 92% w/w sulphuric acid are charged at 70° C. and then 68 g of 92% w/w acetic anhydride are run in at this temperature over 10 min. The reaction medium is maintained at this temperature for 90 min and then rapidly cooled to 35° C. 240 g of hexane are charged with stirring, followed by 220 g of water and by 9 g of 92% w/w $H_2SO_4$. The two phases are separated by settling. The organic phase is then washed with a mixture of 100 g of water and 12 g of 50% NaOH. The organic phase is evaporated on a rotary evaporator at 60° C. under vacuum for 2 h.

After evaporation and partial purification, 237.8 g of 96% w/w tocopheryl acetate (Toco) are obtained (yield=97%).

The aqueous phase (269.7 g), comprising $ZnCl_2$ and HCl, is evaporated on a rotary evaporator under a vacuum of 5 to 10 torr at approximately 115° C. until a suspension is obtained (~90% w/w of $ZnCl_2$). 45.6 g of AcOH are added to this suspension in order to obtain a solution. The exact $ZnCl_2$ assay is quantitatively determined by colorimetry. This $ZnCl_2$ solution is used in the following TMHQ/Isophytol condensation reaction, where the additional water charge is no longer necessary. The amounts of reactants (TMHQ, 36% HCl and isophytol) are calculated on the basis of the amount of $ZnCl_2$ recycled, so as to maintain a $ZnCl_2$/Isophytol molar ratio of 0.72 eq.

The procedures of Examples 21 to 23 are identical to that of Example 20.

TABLE 5

Recycling of $ZnCl_2$.

| Example | Recycling | Maintenance time (min) | AcOH (g) | TMHQ (eq) | $ZnCl_2$ (eq)* | Acid (eq) | T (° C.) | Total $H_2O$** (mol/mol $ZnCl_2$) | Toco assay (%) | Toco Yd (% pure/pure) |
|---|---|---|---|---|---|---|---|---|---|---|
| 20 | 0 | 50 | 45 | 1.01 | 0.73 | 36% HCl (0.09) | 62 | 1.16 | 96*** | 97 |
| 21 | 1 | 50 | 45.6 | 1.01 | 0.73 | 36% HCl (0.09) | 62 | 1.14 | 95.6*** | 97.2 |
| 22 | 2 | 50 | 43.6 | 1.01 | 0.70 | 36% HCl (0.09) | 62 | 1.25 | 95.3*** | 97.2 |
| 23 | 3 | 50 | 42.75 | 1.01 | 0.68 | 36% HCl (0.09) | 62 | 1.34 | 95.8*** | 97.2 |

*the equivalents are in moles with respect to the number of moles of isophytol
**total $H_2O$ = $H_2O$ + $H_2O$ present in the acid
***After partial purification Acetylation catalysts: Influence on the coloration of the tocopheryl acetate (Toco)

Examples 24 to 26

The procedure and the charges of the TMHQ/Isophytol condensation are identical to those in Example 16.

Only the acetylation stage is changed. The parameters are shown in Table 6.

TABLE 6

Influence of the acetylation catalyst on the Toco coloration

| Example | Catalyst | Cata. eq. (mol %) | $Ac_2O$ (eq) | T (°C.) | Time for running in $Ac_2O$ (min) | Maintenance time (min) | Toco assay (%) | Toco Yd (% pure/pure) |
|---|---|---|---|---|---|---|---|---|
| 24 | 92% $H_2SO_4$ | 2 | 1.3 | 70 | 7 | 90 | 89.9 | 97.5 |
| 25 | 85% $H_3PO_4$ | 2 | 1.3 | 95 | 7 | 90 | 89.14 | 96.6 |
| 26 | AcONa | 10 | 1.3 | 110 | 7 | 90 | 89.43 | 98.6 |

The Toco colorations in solution were measured by the Gardner method.

The Toco samples were diluted in cyclohexane. The solution is introduced into a 10 mm quartz cell. The analysis is carried out in the 400–700 nm spectral range.

The trichromatic coordinates are as follows:

| Catalyst | x | y | Y |
|---|---|---|---|
| $H_2SO_4$ | 0.5452 | 0.4325 | 0.84 |
| $H_3PO_4$ | 0.4553 | 0.4596 | 40.67 |
| AcONa | 0.4424 | 0.4594 | 67.71 |

The representation of these points on the corresponding Gardner curve is as follows:

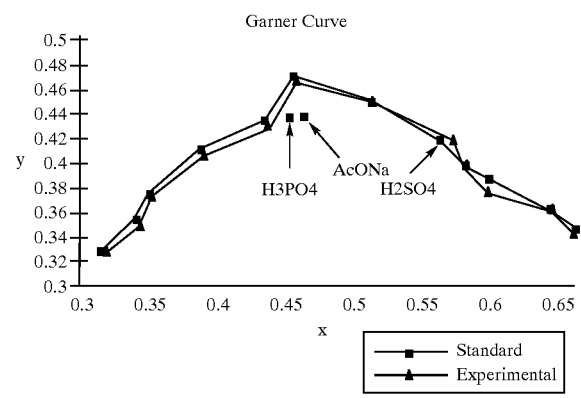

The curve shows that $H_3PO_4$ and AcONa result in products which are less coloured than $H_2SO_4$.

What is claimed is:

1. Process for the preparation of α-tocopherol acetate, comprising: in a first stage, a hydrogenation of trimethylbenzoquinone in a solvent chosen from alkyl acetates comprising 2 to 4 carbon atoms in the alkyl chain is carried out with a supported hydrogenation catalyst chosen from palladium and platinum to form trimethylhydroquinone, in a second stage, after filtration to remove the catalyst of the first stage, the trimethylhydroquinone obtained in the first stage is subjected to a condensation reaction with a phytol in a polar solvent of the ester type and in the presence of a Bronsted acid and of a zinc halide, wherein the condensation reaction is carried out in the presence of an amount of water of between 0.7 molar eq. and 2 molar eq. with respect to the number of moles of zinc halide used and in the presence of an amount of zinc halide of greater than 0.3 molar equivalent with respect to the phytol, said condensation reaction resulting in a second stage reaction medium containing α-tocopherol, in a third stage, the zinc halide is extracted from the second stage reaction medium with water to form an aqueous solution containing the zinc halide and an organic phase containing the α-tocopherol, the aqueous solution is then concentrated under warm conditions so as to leave remaining only at most two moles of water per mole of zinc halide before the aqueous solution is recycled to the second stage of the process, in a fourth stage, the organic phase is concentrated to dryness, so as to remove the polar solvent and its possible byproducts from the α-tocopherol, said α-tocopherol then being acetylated neat under warm conditions by forming an acetylation reaction medium comprising, the α-tocopherol, acetic anhydride, and either an inorganic acid chosen from sulphuric acid or phosphoric acid or an alkaline acetate, said acetylation reaction medium containing no solvent.

2. Process according to claim 1, wherein the amount of zinc halide is between 0.7 and 1.2 molar eq. with respect to the phytol.

3. Process according to claim 1, wherein the zinc halide is zinc chloride.

4. Process according to claim 1, wherein the polar solvent used in the second stage is selected from alkyl acetates comprising 2 to 4 carbon atoms in the alkyl chain.

5. Process according to claim 1, wherein the Bronsted acid is selected from hydrochloric acid or sulphuric acid.

6. Process according to claim 5, wherein the molar amount of Bronsted acid is between 4% and 16% with respect to the number of moles of phytol.

7. Process according to claim 1, wherein the condensation reaction is performed in the presence of an organic acid.

8. Process according to claim 7, wherein the amount by weight of said organic acid is between 3 and 20 times the amount by weight of water present during the condensation reaction.

9. Process according to claim 7, wherein the organic acid is acetic acid.

10. Process according to claim 1, wherein the phytol is isophytol.

11. Process according to claim 1, wherein 0.7 to 2 molar % of sulphuric acid is used as the inorganic acid in said acetylation step.

12. Process according to claim 1, wherein 1 to 2 molar % of phosphoric acid is used as the inorganic acid in said acetylation step.

13. Process according to claim 1, wherein an alkaline acetate is used in said acetylation step and said alkaline acetate is sodium acetate in an amount of 5 to 10 molar %.

14. Process according to claim 1, wherein the α-tocopherol acetate is extracted from the acetylation reaction medium after said acetylation step by: (a) adding a solvent which is immiscible or virtually immiscible with water to the acetylation reaction medium to form a first mixture; (b) washing the first mixture with an acid solution to hydrolyze any remaining acetic anhydride; (c) washing the first mixture with an alkaline medium to deacetylate the trimethylhydroquinone acetates; (d) separating the first mixture, after the washing steps, into an aqueous phase comprising an alkaline salt of trimethylhydroquinone and an organic phase containing the solvent from step (a) and α-tocopherol; (e) removing the solvent from step (a) to obtain the α-tocopherol.

15. Process according to claim 14, wherein the aqueous phase comprising an alkaline salt of trimethylhydroquinone is acidified in the presence of the solvent from the first stage of the process, which extracts the trimethythydroquinone from the aqueous phase, and then the solvent containing the trimethylhydroquinone is recycled to the condensation stage.

* * * * *